United States Patent [19]

Carlin et al.

[11] Patent Number: 5,100,650
[45] Date of Patent: Mar. 31, 1992

[54] ANTI-BACTERIAL ORAL COMPOSITION CONTAINING BIS-BIGUANIDO HEXANES

[75] Inventors: Edward J. Carlin, Secaucus; Anil K. Talwar, Long Valley; Linda T. Principe, Morris Plains; Steven S. Dills, Wharton, all of N.J.

[73] Assignee: Warner-Lambert Company, Morris Plains, N.J.

[21] Appl. No.: 68,468

[22] Filed: Jun. 30, 1987

[51] Int. Cl.$^5$ .................................................. A61K 7/18
[52] U.S. Cl. ...................................... 424/52; 424/49; 424/54; 424/58; 514/901
[58] Field of Search ..................... 424/49, 52, 58, 54; 514/901

[56] References Cited

U.S. PATENT DOCUMENTS

| | | | |
|---|---|---|---|
| 3,976,765 | 8/1976 | Nachtigal | 424/54 |
| 4,157,387 | 6/1969 | Benedict | 424/54 |
| 4,528,180 | 7/1985 | Schaeffer | 424/52 |

FOREIGN PATENT DOCUMENTS 57-212005 12/1982 Japan.
122417 7/1984 Japan.

*Primary Examiner*—F. T. Moezie
*Attorney, Agent, or Firm*—Carl W. Battle; Charles A. Gaglia, Jr.

[57] ABSTRACT

The invention provides an anti-bacterial oral composition such as mouthrinse which includes a bis-biguanido hexane compound such as chlorhexidine and compounds thereof, certain non-ionic surfactants which are poly(oxyethylene)-poly(oxypropylene) block copolymers having an HLB of between 10 and 30 or an ethoxylated hydrogenated caster oil containing from about 10 to 200 moles of added ethylene oxide and sorbitol in high concentrations. The oral composition is found to increase the activity of the bis-biguanido compound from 25% to 150%.

15 Claims, No Drawings

ANTI-BACTERIAL ORAL COMPOSITION CONTAINING BIS-BIGUANIDO HEXANES

BACKGROUND OF THE INVENTION

This invention is concerned with an anti-bacterial oral composition containing a bis-biguanido hexane compound such as chlorhexidine and derivative compounds thereof which markedly enhances the activity of the bis-biguanido hexane compound.

Bis-biguanido hexane compounds such as chlorhexidine and its salts are well known in the art for their anti-bacterial activity and have been used in aqueous-based oral compositions to counter dental plaque and caries formation by bacteria in the oral cavity. Chlorhexidine is active against a wide range of gram-positive and gram-negative organisms, yeast, fungi, facultative anaerobes and aerobes.

Chlorhexidine is a strong base and is most stable in the form of its salts. The most common derivative is the digluconate salt because of its high water-solubility. Chlorhexidine, however, is a very reactive compound and hence its combination with other constituents in oral compositions often results in salt-formation, precipitation and other undesirable effects which reduce its activity or the commercial acceptability of the composition. Oral preparations such as mouthrinses contain water-alcohol mixtures as the oral vehicle, colorants, natural and artificial sweeteners, flavorants, buffers, surfactants and other additives. Many of these preparations have been demonstrated to be unacceptable because one or more of the additives therein either react with chlorhexidine, reduce its activity or form other undesirable products. For example, saccharin forms salts with chlorhexidine and reduces it's activity; buffers such as citrates and phosphates form insoluble salts with chlorhexidine; acesulfame K causes precipitation of chlorhexidine in the oral vehicle; and flavorants such as cinnamic aldehyde react with the amino groups of chlorhexidine to form Schiff bases. Solvents such as polyethylene glycol also inactivate chlorhexidine.

Surfactants have also been employed in oral preparations containing chlorhexidine primarily to solubilize the lipophilic flavorants contained therein. Without a surfactant an opaque formulation results rendering the preparation commercially unacceptable. However, many surfactants deactivate chlorhexidine and are therefore unsuitable.

In Japanese Application No. 57-212005, published June 12, 1984, a composition for oral use is provided including a bis-biguanido hexane such as chlorhexidine and a non-ionic surfactant which prevents the deactivation of chlorhexidine by the surfactant. This prevention is accomplished by the addition to the composition of a higher alcohol such as a fatty acid alcohol having from 10 to 20 carbon atoms. Such alcohols include lauryl alcohol, myristyl alcohol, cetyl alcohol and stearyl alcohol which are used in amounts ranging from 0.1% to 10% by weight of the composition. The non-ionic surfactants include saccharides such as sucrose, maltose, maltitol and lactitol or a free fatty acid ester of a saccharide alcohol such as sucrose fatty acid ester. The compositions may also include minor amounts of other ingredients such as phosphate buffers, cellulose derivatives, flavorants, enzymes, fluorides, and sorbitol.

The present invention, however, provides an oral preparation containing chlorhexidine and derivative compounds in combination with certain selected non-ionic surfactants and sorbitol in relatively high concentrations which increases the bioavailability or activity of the chlorhexidine without the necessity or desirability of higher alcohol additions.

SUMMARY OF THE INVENTION

The present invention provides an anti-bacterial oral composition such as a mouthrinse containing a bis-biguanido hexane compound including chlorhexidine and its derivative compounds which enhances the activity of the bis-biguanido hexane compound from 25% to 150%.

The oral composition includes therein a non-ionic surfactant selected from the group consisting of a poly-(oxyethylene)-poly(oxypropylene) block copolymer having an HLB of between 10 and 30 and an ethoxylated hydrogenated castor oil containing from about 10 to 200 moles of added ethylene oxide and mixtures thereof.

Sorbitol is also added to the composition in amounts ranging from 25% to 75% by weight of total volume of composition based on a sorbitol solution in water containing 70% solids, USP. The composition may contain additional additives such as colorants, flavorants, sweeteners and the like.

DETAILED DESCRIPTION OF THE PREFERRED EMBODIMENTS

The present invention is based upon the discovery that chlorhexidine formulations containing certain non-ionic surfactants and relatively high concentrations of sorbitol actually increase the activity of the chlorhexidine.

The non-ionic surfactants employed are poly(oxyethylene)-poly(oxypropylene) block copolymers. Such copolymers are known commercially as poloxamers and are produced in a wide range of structures and molecular weights with varying contents of ethylene oxide and propylene oxide. The non-ionic poloxamers according to the invention are non-toxic and acceptable as direct food additives. They are stable and readily dispersible in aqueous systems and are compatible with a wide variety of formulating ingredients for oral preparations. The surfactants should have an HLB (Hydophilic-Lipophilic Balance) of between about 10 and 30 and preferably between 10 and 25.

Surfactants useful in this invention include poloxamers:

| | | |
|---|---|---|
| 105 | 188 | 284 |
| 108 | 215 | 288 |
| 123 | 217 | 334 |
| 124 | 234 | 335 |
| 183 | 235 | 338 |
| 184 | 237 | 407 |
| 185 | 238 | |

Generally these polymers should constitute from 0.2% to 2% by weight of total volume of liquid oral preparation (% w/v) and preferably from 0.5% to 1% w/v. A particularly preferred poloxamer is Poloxamer 407 having n HLB of about 22. Such a polymer is sold under the trademark Pluronic F-127 (BASF-WYANDOTTE).

Another class of non-ionic surfactants useful in this invention are ethoxylated hydrogenated castor oils. Such surfactants are prepared by hydrogenating castor oil and treating the so-formed product with from about 10 to 200 moles of ethylene glycol. They are designated as PEG (numeral) hydrogenated castor oil in accordance with the dictionary of the Cosmetics, Toiletries and Fragrance Association, 3rd Ed. wherein the numeral following PEG indicates the degree of ethoxylation, i.e. the number of moles of ethylene oxide added. Suitable PEG hydrogenated castor oils include PEG 16, 20, 25, 30, 40, 50, 60, 80, 100 and 200. The ethoxylated hydrogenated castor oils are used in the same concentrations as the above described poly(oxyethylene)-poly(oxypropylene) block copolymers.

Non-ionic surfactants which are not effective in this invention are those having an HLB outside the stated ranges and non-ionic surfactants such as polyoxyethylene derivatives of sorbitol fatty acid esters since they decrease the activity of chlorhexidine. These surfactants constitute polyoxyethylene derivatives of mixtures of partial esters of sorbitol and its anhydrides.

The liquid oral preparation according to the invention also contain sorbitol solution in high weight to volume concentrations, i.e. from about 25% to 75% w/v and preferably from about 50% to 60% based on a solution of sorbitol in water containing 70% solids, USP. Sorbitol provides sweetness and body to the formulation and a desirable mouth feel, that is, it prevents a harsh taste and assists in providing a fresh and lively sensation in the mouth. It also aids in enhancing flavor. Alhough it is not completely understood it is believed that the sorbitol also aids in the increase in activity of the chlorhexidine in the presence of the surfactant.

Any nontoxic, antibacterial, water-soluble salt of the bis-biguanido hexanes may be employed in the present invention. The preferred bis-biguanido hexanes are 1,6-di(p-chlorophenylbiguanido)hexane, octenidine and 1,6-bis (2-ethyl-hexylbiguanido)hexane. The preferred acid addition salts are the digluconate, diacetate, dihydrogen halides such as fluoride, chloride and bromide, diaminofluorophosphate, and the like.

In the present invention, the bis-biguanido hexane is present in amounts from about 0.01% to about 10% by weight of the total volume of formulation. Preferably the bis-biguanido hexane is present in amounts from about 0.05% to about 1% by weight of the total volume and most preferably from about 0.05% to about 0.5%. The preferred bis-biguanido hexane is 1,6-di(p-chlorophenylbiguanido)-hexane which is chlorhexidine. The preferred salt is the digluconate.

In one form of the invention, the oral preparation may be a liquid such as a mouthwash, spray or rinse. In such a preparation the vehicle is typically a water-alcohol mixture. Generally the ratio of total water to alcohol is in the range of from about 1:1 to about 20:1, preferably about 3:1 to about 20:1 and most preferably about 3:1 to about 10:1 by weight. The total amount of water-alcohol mixture in a mouthwash preparation is typically in the range from about 45% to about 82.5% by weight of the composition. The pH value of such mouthwash preparations is generally from about 4 to about 9 and preferably from about 5 to about 7. A pH below 4 is irritating to the oral cavity and a pH greater than 9 results in an unpleasant mouth feel.

Fluorine providing compounds may be present in the oral preparations of this invention. These compounds may be slightly water soluble or may be fully water soluble and are characterized by their ability to release fluoride ions or fluoride containing ions in water. Typical fluorine providing compounds are inorganic fluoride salts such as soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono- and difluorophosphate and fluorinated sodium calcium pyrophosphate.

Alkali metal, tin fluoride and monofluorophosphates such as sodium and stannous fluoride, sodium monofluorophosphate and mixtures thereof are preferred.

In an oral liquid preparation such as a mouthwash, the fluorine providing compound is generally present in an amount sufficient to release up to about 0.15%, preferably about 0.001% to about 0.1% and most preferably from about 0.001% to about 0.05% fluoride by weight of the preparation.

The oral preparation of the present invention may also contain additional flavorants and colorants.

In the instance where auxiliary sweeteners are utilized, the present invention contemplates the inclusion of those sweeteners well known in the art, including both natural and artificial sweeteners. Thus, additional sweeteners may be chosen in minor amounts from the following non-limiting list provided they do not inactivate the chlorhexidine.

A. Water-soluble sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as xylitol, mannitol and mixtures thereof.

B. Water-soluble artificial sweeteners such as the soluble cyclamate salts and the like.

C. Dipeptide based sweeteners such as L-phenylalanine methyl ester and materials described in U.S. Pat. No. 3,492,131 and the like.

In general, the amount of sweetener will vary with the desired amount of sweeteners selected for a particular oral preparation. This amount will normally be 0.01% to about 40% by weight. The water-soluble sweeteners described in category A above, are preferably used in amounts of about 5% to about 40% by weight, and most preferably from about 10% to about 20% by weight of the final composition. In contrast, the artificial sweeteners described in categories B and C are used in amounts of about 0.005% to about 5.0% and most preferably about 0.05% to about 2.5% by weight of the final composition. These amounts are ordinarily necessary to achieve a desired level of sweetness independent from the flavor level achieved from flavorants.

Suitable flavorings include both natural and artificial flavors, and mints such as peppermint and spearmint. Citrus flavors such as orange and lemon, various fruit flavors, both individual and mixed, and the like are contemplated. Aldehyde-containing flavors are to be avoided as aldehydes generally react with chlorhexidine to form Schiff bases. The flavorings are generally utilized in amounts that will vary depending upon the individual flavor, and may, for example, range in amounts of about 0.05% to about 6% by weight of the final composition.

The colorants useful in the present invention include the pigments which may be incorporated in amounts of up to about 2% by weight of the composition. Also, the and cosmetic applications, known as FD & C and D & C dyes. The materials acceptable for the foregoing spectrum of use are preferably water-soluble. Illustrative examples include the yellow dye, known as D & C Yellow #10, and the dye known as FD & C Green #3 which comprises a triphenylmethane dye. A full recitation of all FD & C and D & C colorants useful in the present invention and their corresponding chemical structures may be found in the Kirk-Othmer Encyclopedia of Chemical Technology, 3rd Edition, in Volume 6, at pages 561-595, which text is accordingly incorporated herein by reference.

The oral preparations of this invention may also be substantially solid or pasty in character such as a dental cream, toothpaste or a toothpowder. Solid or pasty oral preparations contain polishing materials. Typical polishing materials are abrasive particulate materials having particle sizes of up to about 20 microns. Nonlimiting illustrative examples include: water-insoluble sodium metaphosphate, potassium metaphosphate, tricalcium phosphate, dihydrated calcium phosphate, calcium pyrophosphate, magnesium orthophosphate, trimagnesium phosphate, calcium carbonate, alumina, aluminum silicate, zirconium silicates, silica, bentonite, and mixtures thereof. Polishing materials are generally present in an amount from about 20% to about 82% by weight of the oral preparation. Preferably, they are present in amounts from about 20% to about 75% in toothpaste, and from about 70% to about 82% in toothpowder. For toothpaste and dental creams the water content is about 25% to 50% by weight.

The polishing materials are preferably coated with a cationic water soluble polymer to make the polishing material less adsorptive to bis-biguanido hexane compounds. Typical cationic polymers are disclosed in U.S. Pat. No. 4,157,387, the entire contents of which are hereby incorporated by reference. Exemplary polymers are polyacryloxyalkyl ammonium salts; polymethacryloxyalkyl ammonium salts; polyacryloamido alkyl ammonium salts; polyalkenyl ammonium salts; polyvinyloxy ammonium salts; polyvinylbenzyl ammonium salts; polydiallyl ammonium salts; polyvinyl pyridinium ammonium salts; polyvinylimidazolium salts; polyalkylation quaternaries; poly condensation quaternaries; and mixtures thereof.

In clear gels, a polishing agent of colloidal silica and alkali metal aluminosilicate complexes are preferred since they have refractive indicies close to the refractive indicies of gelling agent liquid systems commonly used in dentifrices.

In general, the compositions of the present invention are prepared as follows. The non-ionic surfactant is dissolved in water to form a solution. Sorbitol or sorbitol solution is added to the surfactant solution with mixing until dissolved. Chlorhexidine is added to the solution and mixed until dissolved. Then sufficient water, alcohol or mixtures thereof are added with mixing until the final solution volume is reached. When colorants, auxiliary sweeteners and similar additives are included in the product of the invention, they are added at the same time sorbitol is added. In a preferred embodiment the chlorhexidine is added as the final ingredient. Adding chlorhexidine at an earlier stage in the process exposes the chlorhexidine to concentrated solutions of surfactant, colorant, flavorant and the like which may act on the chlorhexidine to reduce the anti-bacterial activity of the final product.

Flavors may be added to the surfactant-sorbitol solution by first dissolving the flavor in alcohol, then adding the alcoholic solution slowly to the surfactant-sorbitol solution. When non-alcoholic products are prepared the flavors are dissolved directly into the surfactant solution The compositions of the present invention are prepared at ambient temperatures. Heated solutions are to be avoided as they may cause degradation and loss of some 7 of the components.

The present invention is further illustrated by the following examples.

EXAMPLES 1-4

This Example desmonstrates the preparation and activity of a mouthrinse according to the invention containing chlorhexidine gluconate, a non-ionic surfactant and sorbitol.

Exactly 7.00 g of a poly(oxyethylene)-poly(oxypropylene) block copolymer surfactant having a molecular weight of from about 11,500 to 12,500 (PLURONIC F-127 BASF Wyandotte) was dissolved in 350 ml of deionized water. To this solution was added 500.000 g of an aqueous sorbitol solution containing 70% solids by weight, USP, 0.002 g of a yellow food grade dye (D&C Yellow #10) 0.002 g of a green food grade dye (FD&C Green #3) and mixed until dissolved. In a separate step, 0.242 g of a peppermint oil (Peppermint Oil, USP, Redistilled Rose Mitcham) was dissolved in 126.381 ml of an alcohol solution containing 125.000 ml of 95% alcohol and 0.938 g of additional peppermint oil bringing the total peppermint oil weight to 1.1800 g. The alcoholic peppermint oil solution was slowly added with rapid mixing to the aqueous surfactant-sorbitol solution. To this combination was added 6.240 ml a 20% aqueous solution of chlorhexidine gluconate with thorough mixing. Deionized water was added to bring the total volume to 1.000 liter. The preparation was filtered through a Pall 20 micron filter and stored in a glass container. The preparation was clear and green in appearance, had a mint odor and mint taste and a pH of between 5.0 and 7.0.

Table 1 below summarizes the ingredients, the percent weight on a volume basis (% w/v) and the amount of each ingredient in g, ml or l.

TABLE 1

| Ingredient | % w/v | Amount |
|---|---|---|
| 1. Non-ionic Surfactant | 0.700 | 7.000 g |
| 2. Sorbitol Solution (70% solids) | 50.0000 | 500.000 g |
| 3. Green Dye | 0.0002 | 0.002 g |
| 4. Yellow Dye | 0.0002 | 0.002 g |
| 5. Peppermint Oil | 0.1180 | 1.180 g |
| 6. Alcohol Solution | 12.6381* | 126.381 ml |
| 7. Chlorhexidine Gluconate | 0.1248 | 1.248 g |
| 8. Deionized Water | add to adjust water to | 1.000 l |

*v/v

In similar experimental preparations (Ex. 2, 3 & 4) mouthrinses were prepared which contained 0.10, 0.08 and 0.06 % w/v of chlorhexidine gluconate, respectively. A control mouthrinse preparation was formulated containing no chlorhexidine gluconate.

Examples 1 to 4 and the control were subjected to a microbiological assay for chlorhexidine gluconate (CHX). Table 2 below shows the corresponding percentage of available chlorhexidine gluconate (corres. % available CHX) for each example as a measure of increased or decreased chlorhexidine activity.

TABLE 2

| Exp. No. | % CHX | corres. % available CHX | % of theory |
|---|---|---|---|
| CONTROL | 0 | 0 | — |
| 1 | 0.12 | 0.30 | 250 |
| 2 | 0.10 | 0.28 | 280 |
| 3 | 0.08 | 0.10 | 125 |
| 4 | 0.06 | 0.06 | 100 |

As Table 2 indicates, in Examples 1 to 3 chlorhexidine gluconate activity was enhanced 25% to 150%. In Example 4 activity was maintained.

What is claimed is:

1. An anti-bacterial liquid oral composition having enhanced antibacterial activity comprising a liquid oral vehicle, from about 0.1% to 10% by weight of total volume of said composition of an anti-bacterial bis-biguanido hexane compound, from 0.2% to 2% by weight of total volume of a non-ionic surfactant selected from the group consisting of a poly(oxyethylene)-poly (oxypropylene) block copolymer having an HLB of between 10 and 30 and an ethoxylated hydrogenated castor oil containing from about 10 to 200 moles of added ethylene oxide and mixtures thereof and from 25% to 75% by weight of total volume of solution of sorbitol in water based on a 70% solids solution, said sorbitol and non-ionic surfactant being present in an amount effective to increase the activity of the bis-biguanido compound and wherein the pH of the composition is from about 4 to about 9.

2. The oral composition of claim 1 wherein said oral vehicle is water.

3. The liquid oral composition of claim 1 which comprises a mouthrinse.

4. The liquid oral composition of claim 1 wherein said oral-vehicle is an alcohol-water mixture.

5. The liquid oral composition of claim 1 wherein said bis-biguanido hexane compound is chlorhexidine gluconate.

6. The oral composition of claim 1 wherein said poly-(oxyethylene)-poly(oxypropylene) block copolymer has an HLB of between 20 and 25.

7. The oral composition of claim 1 wherein said poly-(oxyethylene)-poly(oxypropylene) block copolymer has an HLB of about 22.0.

8. The oral composition of claim 1 which further comprises a flavorant.

9. The oral composition of claim 1 which further comprises a colorant.

10. The oral composition of claim 1 which comprises an oral spray.

11. The liquid oral composition of claim 1 which further comprises a fluoride providing compound.

12. A liquid anti-bacterial oral mouthwash composition having enhanced antibacterial activity comprising an alcohol-water mixture, from about 0.1 to 1% by weight of total volume of a chlorhexidine compound, from 0.2 to 2% by weight of total volume of a poly (oxyethylene) - poly (oxypropylene) block copolymer having an HLB of from about 20 to 25 and from 50% to about 60% by weight of total volume of a solution of sorbitol in water based on a 70% solids solution, said block copolymer and sorbitol being present in an amount effective to increase the activity of the chlorhexidine compound and wherein the pH of the composition is from about 4 to about 9.

13. The oral composition of claim 12 wherein said block copolymer has an HLB of about 22.

14. The oral composition of claim 12 which comprises a mouthrinse.

15. The oral composition of claim 12 wherein said chlorhexidene compound is chlorhexidine gluconate.

* * * * *